(12) United States Patent
Zhai et al.

(10) Patent No.: US 10,258,413 B2
(45) Date of Patent: Apr. 16, 2019

(54) HUMAN ORGAN MOVEMENT MONITORING METHOD, SURGICAL NAVIGATION SYSTEM AND COMPUTER READABLE MEDIUM

(71) Applicant: Tsinghua University, Beijing (CN)

(72) Inventors: Weiming Zhai, Beijing (CN); Yixu Song, Beijing (CN)

(73) Assignee: Tsinghua University, Beijing (CN)

( * ) Notice: Subject to any disclaimer, the term of this patent is extended or adjusted under 35 U.S.C. 154(b) by 22 days.

(21) Appl. No.: 15/106,746

(22) PCT Filed: Jun. 18, 2014

(86) PCT No.: PCT/CN2014/080237
§ 371 (c)(1),
(2) Date: Jun. 20, 2016

(87) PCT Pub. No.: WO2015/188393
PCT Pub. Date: Dec. 17, 2015

(65) Prior Publication Data
US 2017/0215969 A1  Aug. 3, 2017

(30) Foreign Application Priority Data

Jun. 11, 2014 (CN) .......................... 2014 1 0259145

(51) Int. Cl.
*A61B 5/00* (2006.01)
*A61B 5/08* (2006.01)
(Continued)

(52) U.S. Cl.
CPC .............. *A61B 34/20* (2016.02); *A61B 5/002* (2013.01); *A61B 5/0013* (2013.01); *A61B 5/08* (2013.01);
(Continued)

(58) Field of Classification Search
None
See application file for complete search history.

(56) References Cited

U.S. PATENT DOCUMENTS

| 2004/0034297 A1 | 2/2004 | Darrow et al. |
| 2007/0167712 A1 | 7/2007 | Keglovich et al. |
| 2013/0223702 A1* | 8/2013 | Holsing ................. A61B 5/113 382/128 |

FOREIGN PATENT DOCUMENTS

| CN | 1806771 A | 7/2005 |
| CN | 2748042 Y | 12/2005 |

(Continued)

OTHER PUBLICATIONS

Weiming Zhai, "Research on Image Guided Computer-Assisted Intervention Surgery Navigation", Dissertation for Doctor of Engineering, Tsinghua University, Dec. 2010.
(Continued)

*Primary Examiner* — Idowu O Osifade
(74) *Attorney, Agent, or Firm* — Sheppard Mullin Richter & Hampton LLP

(57) ABSTRACT

The present disclosure provides a human organ movement monitoring method for monitoring human organ movement in a surgical process in real time and a surgical navigation system. The human organ movement monitoring method includes: obtaining first position and orientation of movement monitoring tools in an image coordinate system identified from a preoperative three-dimensional medical image; determining second position and orientation of the movement monitoring tools in a positioning coordinate system in the surgery in real time; calculating an optimal coordinate transformation relation between the positioning coordinate system and the image coordinate system in real time based on the first position and orientation of the movement monitoring tools in the image coordinate system and the second (Continued)

position and orientation thereof in the positioning coordinate system, and calculating overall errors of coordinate transformation of the movement monitoring tools from the positioning coordinate system to the image coordinate system based on the optimal coordinate transformation relation; and evaluating movement degree of a human organ at various moments relative to a preoperative scanning moment based on the real-time determined overall errors of coordinate transformation of the movement monitoring tools at the various moments.

14 Claims, 4 Drawing Sheets

(51) Int. Cl.
| | | |
|---|---|---|
| *A61B 5/11* | (2006.01) | |
| *G06T 7/73* | (2017.01) | |
| *A61B 17/00* | (2006.01) | |
| *A61B 34/10* | (2016.01) | |
| *A61B 34/20* | (2016.01) | |
| *A61B 90/00* | (2016.01) | |
| *G06F 19/00* | (2018.01) | |
| *G06T 7/246* | (2017.01) | |

(52) U.S. Cl.
CPC ............ *A61B 5/1107* (2013.01); *A61B 34/10* (2016.02); *A61B 90/00* (2016.02); *G06F 19/00* (2013.01); *G06F 19/321* (2013.01); *G06T 7/248* (2017.01); *G06T 7/74* (2017.01); *A61B 2017/00694* (2013.01); *A61B 2017/00699* (2013.01); *A61B 2034/102* (2016.02); *A61B 2034/105* (2016.02); *A61B 2034/2051* (2016.02); *A61B 2034/2055* (2016.02); *A61B 2034/2061* (2016.02); *A61B 2034/2065* (2016.02); *A61B 2034/2074* (2016.02); *A61B 2090/3954* (2016.02); *A61B 2090/3966* (2016.02); *G06T 2207/20221* (2013.01); *G06T 2207/30061* (2013.01); *G06T 2207/30204* (2013.01)

(56) References Cited

FOREIGN PATENT DOCUMENTS

| | | |
|---|---|---|
| CN | 101327148 A | 12/2008 |
| CN | 201353203 Y | 12/2009 |
| CN | 102266250 A | 12/2011 |
| CN | 102525662 A | 7/2012 |
| CN | 202437059 U | 9/2012 |
| CN | 102949240 A | 3/2013 |
| CN | 103356284 | 10/2013 |
| CN | 103356284 B | 9/2015 |

OTHER PUBLICATIONS

International Search Report for Application Np. PCT/CN2014/080237, dated Mar. 18, 2015, 6 pages.
International Preliminary Report on Patentability for International Application No. PCT/CN2014/080237, dated Dec. 15, 2016. (6 pages).
International Search Report for International Application No. PCT/CN2014/080237, English translation, dated Mar. 18, 2015. (10 pages).
Office Action and Search Report for Chinese Application No. 201410259145.3, English Translation, dated Aug. 13, 2015. (18 pages).
Written Opinion for International Application No. PCT/CN2014/080237, English translation, dated Mar. 18, 2015. (15 pages).
Zhai, Weiming, "Research on Image Guided Computer-Assisted Intervention Surgery Navigation", Dissertation submitted to Tsinghua University for the degree of Doctor of Engineering, Dec. 2010.

* cited by examiner

HUMAN ORGAN MOVEMENT MONITORING METHOD, SURGICAL NAVIGATION SYSTEM AND COMPUTER READABLE MEDIUM

TECHNICAL FIELD

The present disclosure generally relates to a surgical navigation system and method, and in particular relates to a human organ movement monitoring method for monitoring human organ movement in a medical process in real time, a surgical navigation system and a computer readable medium.

BACKGROUND

An interventional operation is a developed method of modern surgery, the difference of the interventional operation from the traditional surgery lies in that no surgical operation is needed, a special surgical instrument, such as a catheter, a frozen needle, a radio frequency ablation needle, a guide wire and the like can be penetrated into a focus location or a surgical target location in vivo through a very small wound, and then a treatment purpose is achieved by a variety of physical/chemical effects, so as to solve the problems of tumor excision, biopsy, artificial equipment placement and the like that can be solved only by open surgery previously.

In an interventional operation process, a doctor cannot directly observe a treatment site or focus in a patent body and need to rely on computer-assisted surgery navigation technology guided by medical images. The computer-assisted surgery navigation technology is a cross research topic integrating computer science, artificial intelligence, automatic control, image processing, three-dimensional graphics, virtual reality and clinical treatment and other aspects. Multiple modes of medical images are adopted in the surgery navigation technology to assist the doctor to directly penetrate the surgical instrument into the focus for local treatment, so as to improve the surgery quality, reduce surgical trauma and reduce the pain of patients.

Surgical navigation is used for guiding the execution of clinical surgery in real time by means of a medical image of the patient and a three-dimensional model generated thorough reconstruction of the medical image. The medical image data of the patient are obtained, for example, by means of CT (computerized tomography) or MM (Magnetic Resonance Imaging) scanning. A surgical navigation system associates the preoperative medical image data with the intraoperative surgical site of the patient through a positioning device, and can accurately display an anatomical structure of the patient and the details of a three-dimensional spatial position near the focus in a software interface. When the surgical instrument points to any location in the patient body, the coordinate information thereof will be obtained by the navigation system in real time and is displayed on the three-dimensional model of the patient. In this case, even if no surgery under a operation knife is carried out on the patient, the doctor can get the relative position relation of the surgical instrument and the tumor focus in real time.

Compared with the traditional surgical means, the surgical navigation has the following advantages:

1, the focus can be reconstructed in real time through the three-dimensional technology, and the structural features on the surrounding of a surgical field are displayed;

2, the most suitable surgical approach can be selected through a preoperative surgical plan design;

3, possible encountering tissue structures on the surgical approach can be displayed;

4, important tissue structures that should be evaded, for example, blood vessels, nerves, bones and the like can be displayed;

5, a range for treatment of the focus can be displayed;

6, the position and orientation of the surgical instrument can be accurately calculated and displayed in real time;

7, the spatial position relation of the surgical instrument and the focus can be displayed, and the advance direction of the surgical instrument can be indicated; and 8, the surgical approach can be adjusted in the surgery in real time so as to arrive at the focus location more accurately.

For the convenience of description, a CT image is used as an example of the medical image below, but obviously other images, such as an MM image, can also be used as the example of the medical image.

Real-time surgical navigation relates to the use of a positioning device or a tracking system, for example, an electromagnetic (EM, electromagnetic) tracker is used for tracking the distal tip of a surgical tool, such as a puncture needle, so as to associate the position of the surgical tool with the preoperative medical image, for example, the CT image and display a fused image to a clinician. To achieve data integration between a CT space and a tracker space, a registration process based on reference marks is generally carried out before navigation. These reference marks (external reference marks or internal anatomical reference marks) are identified from the CT image, and these reference markers are touched by a calibrated tracking probe to obtain coordinates of these reference markers in the tracker space, which is called a positioning coordinate system below. Thereafter, registration based on points is executed to find a coordinate transformation matrix between the CT space and the tracker space. A registration matrix is obtained through the coordinate transformation matrix, and the registration matrix is used for aligning the surgical tool with the preoperative medical image, so that the image of the surgical tool can be accurately fused with the CT image in a CT coordinate system based on the position information of the surgical tool in the positioning system, and the fused image is visually displayed to the clinician.

SUMMARY

Currently, the surgical navigation technology has been widely used in neurosurgery surgical navigation and orthopedic surgical navigation. However, these surgeries all assume that the human body is a completely stationary rigid body, and this stationary state will maintain from an early CT scanning period to the end of the entire surgical process. Although this assumption can be approximately assumed to be tenable in most neurosurgeries and orthopedic surgeries, it is difficult to be tenable in the field of pleuroperitoneal cavity interventional surgeries. For example, a pleuroperitoneal cavity tissue movement (including a tumor tissue and a normal tissue) caused by breath can generally reach a range of 2-4 cm, while the accuracy of clinical surgery is generally at a millimeter level, and such an error will result in that the currently mainstream surgical navigation systems are difficult to be safely and stably used in the clinical practice of the pleuroperitoneal cavity interventional surgeries.

In view of the above situation, the present disclosure is proposed.

According to one aspect of the present disclosure, a human organ movement monitoring method for monitoring human organ movement in a surgical process in real time is provided, wherein a three-dimensional medical image of a treatment site of a patient fixed with two or more movement monitoring tools is obtained by scanning prior to the surgery, the three-dimensional medical image having an associated image coordinate system, and the human organ movement monitoring method includes the following steps: obtaining first position and orientation of the movement monitoring tools in the image coordinate system identified from the preoperative three-dimensional medical image; in a state that the same movement monitoring tools are fixed on the body of the patient at the same position and orientation as in the preoperative scanning, determining second position and orientation of the movement monitoring tools in a positioning coordinate system in real time, wherein the positioning coordinate system is a coordinate system which is referenced in a process of positioning the position and orientation of a surgical tool; calculating an optimal coordinate transformation relation between the positioning coordinate system and the image coordinate system in real time based on the first position and orientation of the movement monitoring tools in the image coordinate system and the second position and orientation thereof in the positioning coordinate system, and calculating overall errors of coordinate transformation of the movement monitoring tools from the positioning coordinate system to the image coordinate system based on the optimal coordinate transformation relation; and evaluating movement degree of a human organ at various moments relative to a preoperative scanning moment based on the real-time determined overall errors of coordinate transformation of the movement monitoring tools at the various moments.

According to another aspect of the present disclosure, a surgical navigation system is provided, including: a positioning device, used for tracking position and orientation of a surgical tool and movement monitoring tools in a positioning coordinate system; two or more movement monitoring tools, which are fixed on a patient body, and the position and orientation of which in the positioning coordinate system are capable of being tracked by the positioning device; a three-dimensional medical image obtaining unit, used for obtaining a preoperative three-dimensional medical image of a treatment site of a patient fixed with the movement monitoring tools, the three-dimensional medical image having an associated image coordinate system; a surgical navigation workstation, used for registering and combining the preoperative three-dimensional medical image with an intraoperative surgical tool image and visually displaying the same on a connected display device to guide the surgical operation of a surgeon; wherein the surgical navigation workstation further monitors the movement state of a human organ through the following operations: identifying first position and orientation of the movement monitoring tools in the image coordinate system from the preoperative three-dimensional medical image; determining second position and orientation of the movement monitoring tools in the positioning coordinate system in the surgery in real time; calculating an optimal coordinate transformation relation between the positioning coordinate system and the image coordinate system in real time based on the first position and orientation of the movement monitoring tools in the image coordinate system and the second position and orientation thereof in the positioning coordinate system, and calculating overall errors of coordinate transformation of the movement monitoring tools from the positioning coordinate system to the image coordinate system; and evaluating movement degree of the human organ at various moments relative to a preoperative scanning moment based on the real-time determined overall errors of coordinate transformation at the various moments.

According to a further aspect of the present disclosure, a computer readable medium is provided, on which a computer program is recorded, the computer program being used in combination with a surgical navigation system and executing the following operations when being executed by a processing device: obtaining first position and orientation of movement monitoring tools in an image coordinate system identified from a preoperative three-dimensional medical image, wherein the preoperative three-dimensional medical image is obtained by scanning a treatment site of a patient fixed with two or more movement monitoring tools prior to the surgery, the three-dimensional medical image having an associated image coordinate system; in a state that the same movement monitoring tools are fixed on the body of the patient at the same position and orientation as in the preoperative scanning, determining second position and orientation of the movement monitoring tools in a positioning coordinate system in real time, wherein the positioning coordinate system is a coordinate system which is referenced in a process of positioning the position and orientation of a surgical tool; calculating an optimal coordinate transformation relation between the positioning coordinate system and the image coordinate system in real time based on the first position and orientation of the movement monitoring tools in the image coordinate system and the second position and orientation thereof in the positioning coordinate system, and calculating overall errors of coordinate transformation of the movement monitoring tools from the positioning coordinate system to the image coordinate system based on the optimal coordinate transformation relation; and evaluating movement degree of a human organ at various moments relative to a preoperative scanning moment based on the real-time determined overall errors of coordinate transformation of the movement monitoring tools at the various moments.

The surgical navigation system and the human organ movement monitoring method provided by the embodiments of the present disclosure can be used for solving or relieving the problem in pleuroperitoneal cavity surgical navigation that a tumor displacement is caused by a respiratory movement of the human body to reduce the surgical navigation precision, and also simplifying the surgical navigation procedures to facilitate the use and popularization of the surgical navigation in a plurality of fields.

BRIEF DESCRIPTION OF THE DRAWINGS

These and/or other aspects and advantages of the present disclosure will become clearer and more understandable from the following detailed description of the embodiments of the present disclosure in combination with the accompany drawings, wherein.

DETAILED DESCRIPTION

Figure 1:
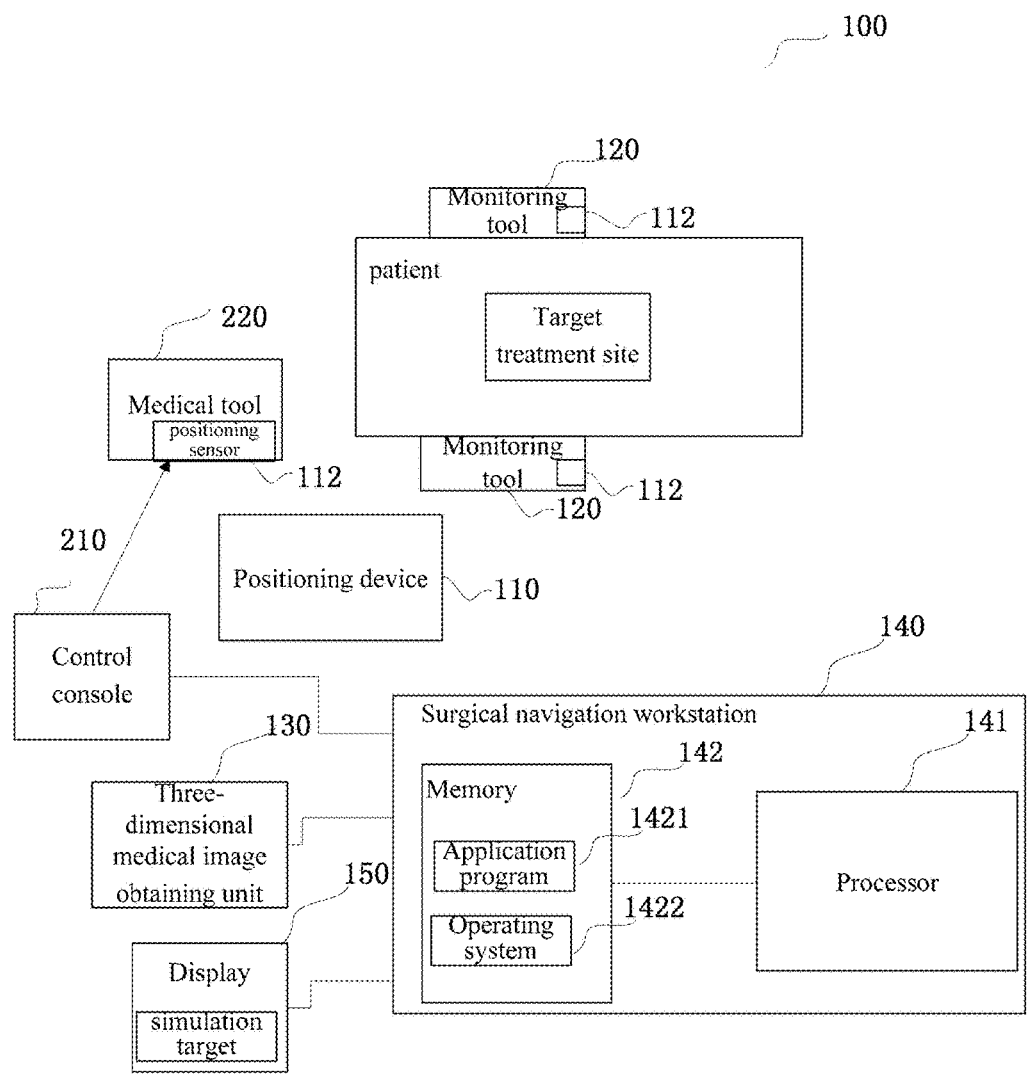
FIG. 1 shows a configuration block diagram of an exemplary surgical navigation system 100 according to an embodiment of the present disclosure.

In order that those skilled in the art can better understand the present disclosure, a further detailed illustration of the present disclosure will be given below in combination with the accompany drawings and specific embodiments.

Before the embodiments of the present disclosure are described in detail below, to facilitate those skilled in the art understanding and mastering the present disclosure, main concept of the present disclosure is described below.

A preoperative CT image is collected at a certain breath state moment or breath state stage of a patient. In a CT scanning process, position and orientation of reference marks in a positioning coordinate system are inconvenient to track in general. A CT scanning moment and an actual surgical moment may be separated for several days.

In a subsequent surgical process, the patent is consistently in a periodic movement process of breath, theoretically only when the breath state of the patient at a certain moment is uniform with or close to that at the preoperative CT scanning moment or stage, the position and orientation of the reference marks in the positioning coordinate system at the moment correspond to the position and orientation of the reference marks in an image coordinate system identified previously from the CT image, so the registration matrix obtained at this time is correct, then the position of a surgical tool can be accurately transformed into a CT space at this moment, and the visual display of a fused three-dimensional model provided for a clinician is accurate.

To this end, the inventor thinks that the position and orientation (orientations or azimuth angles) of monitoring tools (having reference marks thereon) in the positioning coordinate system can be monitored, a uniform coordinate transformation matrix from the positioning coordinate system to a three-dimensional image coordinate system is optimized, the sum of errors (referred to as overall errors below at sometimes) of transformation of the monitoring tools from the positioning coordinate system to the three-dimensional image coordinate system are determined, it is deemed that a moment with a smaller error indicates that the position and orientation of a human organ at this time are close to the position and orientation of the human organ at the CT scanning moment, and the information is visually or aurally provided for the clinician to assist the surgery of the clinician.

It should be noted that, in the following description, lung and related tissue movement caused by a respiratory movement is used as examples of a human organ movement, but the present disclosure is not limited thereto and is suitable for monitoring other processes of dynamic internal movements of a human body, for example, a heartbeat movement. Embodiments described herein can be preferably used for helping to position the lung or tissues close to the lung, but the tissue can also be located at other positions, for example, the heart, digestive organs, blood vessels, the kidney, etc.

In the following description, the position and orientation (orientation) can be expressed by 6 numerical values, namely position coordinates expressing three-dimensional positions and three angle values expressing orientation, and this is called 6D pose in some traditional technologies. However, the position and orientation can be described by fewer values as necessary.

Herein, "registration" indicates establishing a mapping relation or a coordinate transformation relation between two coordinate systems, for example, "registration between the positioning coordinate system and the image coordinate system" indicates establishing a mapping relation between the positioning coordinate system and the image coordinate system or figuring out a coordinate transformation matrix therebetween, and the positioning coordinate system herein is a coordinate system which is referenced by a positioning device when positioning the surgical tool and movement monitoring tools.

FIG. 1 shows a configuration block diagram of an exemplary surgical navigation system 100 according to an embodiment of the present disclosure.

As shown in FIG. 1, the surgical navigation system 100 includes a positioning device 110, two or more movement monitoring tools 120, a three-dimensional medical image obtaining unit 130 and a surgical navigation workstation 140. To conveniently describe the working process of the surgical navigation system 100, FIG. 1 further shows a control console 210 and a medical tool 220, which cooperatively work with the surgical navigation system 100.

The positioning device 110 is configured to track position and orientation of the movement monitoring tools in the positioning coordinate system. As shown in the figure, positioning sensors 112, for example, magnetic induction positioning sensors can be placed on each movement monitoring tool. The positioning device 110 can track the position and orientation of the movement monitoring tools in the positioning coordinate system by means of the magnetic induction positioning sensors.

The positioning device 110 is further configured to track the position and orientation of the surgical tool in a second positioning coordinate system. For example, the surgical tool is a puncture needle, the positioning sensor 112 is installed on the puncture needle, and then, the positioning device 110 can track the position and orientation of the puncture needle by means of the positioning sensor. In an example, one positioning device can track the signals of 8 positioning sensors at the same time.

The positioning device 110 can adopt one of electromagnetic (EM) tracking technology, optical tracking technology and fiber grating tracking technology. As examples of commercially available electromagnetic positioning systems, the Aurora system of the Canada NDI company, the DriveBay of the American Asension company, the PercuNav system of the Dutch Philips company, the InstaTrak3500 plus system of the American GE company, the StealthStation AxiEM system of the American Medtronic company and the Cygnus FPS system of the American Compass company are available.

The two or more movement monitoring tools 120 are configured to be fixed on a patient body at the same position and orientation before the surgery (specifically, before CT scanning) and in the surgery, but before the intervention of the surgical tool. A description is given below by taking it as an example that the monitored movement is a respiratory movement. For the convenience of description, the movement monitoring tools 120 may be called breath monitoring tools below. The wearing positions of the breath monitoring tools on the patient body are places greatly influenced by the breath to the best, so that the relative positions of the several breath monitoring tools may generate relative change to a certain extent with the respiratory movement.

In an example, each movement monitoring tool is provided with at least four mark points capable of being tracked by a positioning device, in which any three arbitrary mark points are non-collinear, wherein the first position and orientation of the movement monitoring tools in the image coordinate system are identified by identifying the mark points of each movement monitoring tool in the three-dimensional medical image; and the second position and orientation of the movement monitoring tools in the positioning coordinate system are determined by tracking the mark points of each movement monitoring tool in the surgery through the positioning device. Here, at least four mark points are arranged on one movement monitoring tool, and any three arbitrary mark points are non-collinear, so that a coordinate transformation matrix from the positioning coordinate system to the image coordinate system can be figured out based on the position and orientation of the at least four mark points in the image coordinate system and the first positioning coordinate system. In an example, for example, the mark points are metal balls for example, and the image parameters of the metal balls in the CT are obviously different from the image parameters of the human body material, thereby capable of being manually identified or automatically identified through image processing easily. For each such breath monitoring tool, a unique coordinate transformation matrix can be determined according to the first position and orientation of the breath monitoring tool in the image coordinate system and the second position and orientation thereof in the positioning coordinate system, and the coordinate transformation matrix can be used for guaranteeing zero transformation error. However, since a plurality of breath monitoring tools are provided, and a single coordinate transformation matrix is used for transforming each one of the plurality of breath monitoring tools from the first position and orientation in the image coordinate system to the second position and orientation in the positioning coordinate system, thus a transformation error will be generated. As mentioned above, the main concept of the present disclosure is to monitor the difference of the poses of the breath monitoring tools relative to the poses at a preoperative CT scanning moment by calculating optimal uniform transformation matrixes at various moments and corresponding overall transformation errors, so as to monitor the difference of the states of the human organ at various moments relative to the state at the preoperative CT scanning moment to achieve the purpose of monitoring the human organ movement.

It should be noted that each breath monitoring tool is not necessarily provided with four or more mark points. On the contrary, as long as the transformation matrix and the overall transformation error between the two coordinate systems can be figured out on the basis of the positions of all mark points of all breath monitoring tools in the positioning coordinate system and the image coordinate system. For example, two breath monitoring tools can be provided, each breath monitoring tool has three mark points, for example, in this way, an optimal coordinate transformation matrix and the corresponding transformation error can be similarly figured out through the positions of the 6 mark points in the positioning coordinate system and the positions thereof in the image coordinate system. As another example, four breath monitoring tools can be provided, each breath monitoring tool has two mark points, in this way, the optimal coordinate transformation matrix and the corresponding transformation error can be similarly figured out through the positions of the eight mark points in the positioning coordinate system and the positions thereof in the image coordinate system. As a more extreme example, 5 breath monitoring tools are provided, each breath monitoring tool has one mark point, in this way, the optimal coordinate transformation matrix and the corresponding transformation error can be similarly figured out through the positions of the 5 mark points in the positioning coordinate system and the positions thereof in the image coordinate system.

Figure 2:
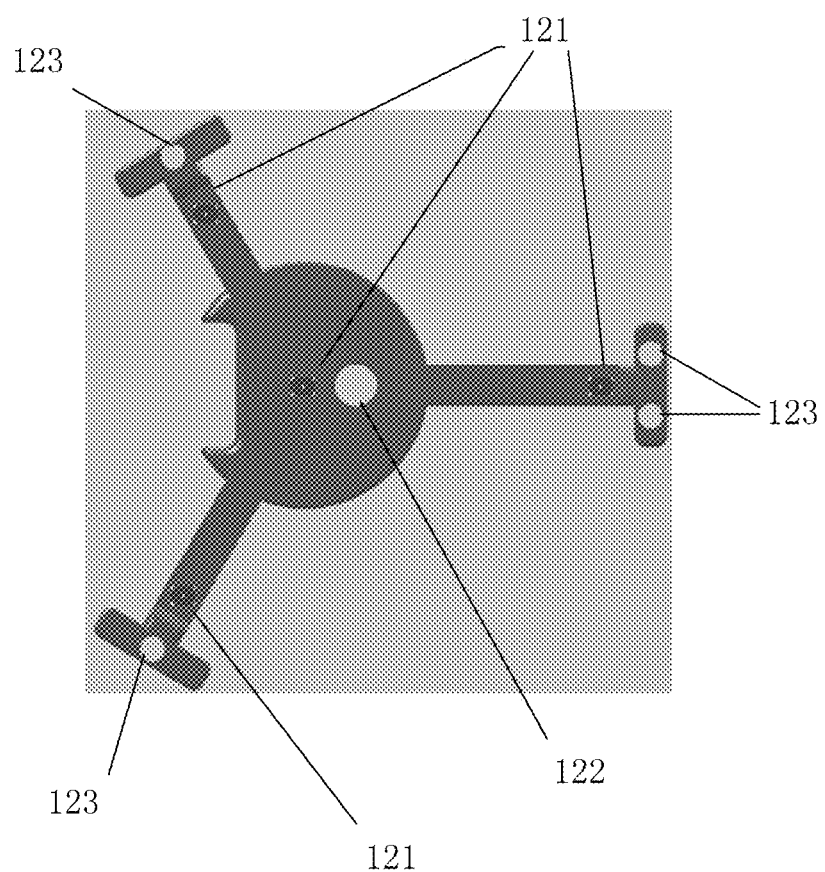
FIG. 2 shows an exemplary structural diagram of a breath monitoring tool 120 according to an embodiment of the present disclosure.

FIG. 2 shows an exemplary structural diagram of a breath monitoring tool 120 according to an embodiment of the present disclosure. The breath monitoring tool 120 can be composed of a plastic framework and an object to be identified. In the plastic framework, 4 image identifiable markers (for example, metal balls, for example, being made of a lead material) are placed at positions indicated by a mark number 121, the image parameters (mainly including CT values and MRI values) of these markers in a CT or MRI image are of obvious distinguishing features in comparison with the image parameters of a peripheral material, so that better development can be obtained in a CT machine, for example, the markers can be extracted using a known method. As another example of the markers, adhesive electrodes adopted in ECG production can be adopted. Identifiable markers can be automatically extracted from the image through subsequent processing of the CT image or the MRI image, and the information (including coordinate information and direction information of a tool center) of the position and orientation (for the convenience of description, can be called pose below) of the tool can be further calculated.

A magnetic induction positioning device can be placed on the facade of the exemplary breath monitoring tool 120 in FIG. 2, and a round hole 122 at the middle and a concave structure at the left side are mainly used for facilitating the disassembly of the magnetic induction positioning device.

Three extended straight rods are mainly used for facilitating attachment on a human body surface, meanwhile, markers 121 capable of being identified by CR or MR can be placed on the rods, and the pose information can be calculated after the markers are identified. A round hole 123 in a small cross bar at the distal tip of each straight rod can be used for recording position information on the human body surface through a marking pen, in this way, after the breath monitoring tool 120 is removed from the surface of the patient, the breath monitoring tool 120 can be accurately adhered on the human body surface again according to the recorded pose information.

The structure and shape of the breath monitoring tool as shown in FIG. 2 are merely exemplary, and the configuration thereof can be changed as needed.

As an example, the utilization process of the breath monitoring tools can be divided into a CT scanning stage and an intraoperative stage. Specifically, before CT scanning is carried out, two or more breath monitoring tools are fixed at the chest position of the patient, the wearing pose information is marked on the human body surface, for example, by using the marking pen, then the patient is pushed into a CT room to carry out the CT scanning to obtain a CT scanning data set, and the position and orientation of the breath monitoring tools can be identified from such CT scanning data set. Incidentally, a three-dimensional model of a related treatment site of the patient can be reconstructed from such CT scanning data set via image processing, and such three-dimensional model can be visualized on the display device and is fused with the image of the tracked surgical tool for display to assist the surgery of the doctor. In the surgery and before the intervention of the surgical tool in vivo, the breath monitoring tools are worn according to the aforementioned pose information recorded on the body surface of the patient, the poses of the breath monitoring tools in the positioning coordinate system are monitored in real time and the coordinate transformation matrix and corresponding overall errors of all breath monitoring tools are optimized to figure out, and the human organ movement is monitored based on the change of the overall errors over time.

The three-dimensional medical image obtaining unit 130 can be a part of the surgical navigation workstation 140 or a separate device. The three-dimensional medical image obtaining unit 130 is used for obtaining a preoperative three-dimensional medical image of a treatment site of the patient fixed with the movement monitoring tools, the three-dimensional medical image having an associated image coordinate system. For example, a three-dimensional data set obtained by preoperative CT scanning is stored in a database, the three-dimensional medical image obtaining unit 130 can be operatively coupled to the database, read a specific three-dimensional data set from the database and visually display the specific three-dimensional data set on the display device through image processing, such as rendering and the like. The three-dimensional medical image obtaining unit 130 can simply read and display a reconstructed three-dimensional model and can also read the non-reconstructed CT scanning data set and reconstruct the CT scanning data set to obtain and display the three-dimensional model. As to the method for reconstructing the three-dimensional model from the CT or MRI data set, reference can be made to related introduction of coordinate transformation and error calculation, for example, reference can be made to introductions in the third chapter and fourth chapter in a doctoral dissertation entitled "RESEARCH ON KEY TECHNOLOGY OF COMPUTER ASSISTED INTERVENTIONAL OPERATION UNDER IMAGE GUIDANCE" of Zhai Weiming, the entire contents of which are herein incorporated by reference.

The control console 210 can be connected to the surgical navigation workstation 140 or is a part of the surgical navigation workstation 140. The control console 210 can receive the pose information of the breath monitoring tools and the pose information of the surgical tool from the positioning device 110. The control console 210 can also send an instruction of operating the puncture needle according to the indication of the clinician.

The surgical navigation workstation 140 is configured to register and combine the preoperative three-dimensional medical image with an intraoperative surgical tool image and visually display the same on the connected display device to guide the surgical operation of a surgeon.

The surgical navigation workstation 140 can include a processor 141 and a memory 142, and an application program 1421 and an operating system 1422 can be stored in the memory 142. The application program 1421 can include a program code, and the program code, when being executed by the processor 141, can execute the human organ movement monitoring method that will be described in detail below. The processor here is a generalized concept and can be implemented by a single dedicated processor, a single shared processor, or a plurality of individual processors, wherein one processor among the processors can be shared, in addition, the use of the word "processor" or "controller" should not be explained as exclusively referring to hardware capable of executing software, but can implicitly include, but not limited to, digital signal processor (DSP) hardware, a read-only memory (ROM) used for storing software and a nonvolatile memory. The surgical navigation workstation 140 can further include an interface used for real-time interaction with a display 150.

The display 150 can display the orientation, shape and/or position or the like of a medical target tissue under the control of the surgical navigation workstation 140, and can also display the fusion of an image of the three-dimensional model of a related position of the patient and an image of the surgical tool.

The surgical navigation workstation 140 can further include man-machine interaction interfaces, for example, being connected to such peripheral devices as a keyboard, a mouse, a touch screen system, etc. The surgical navigation workstation 140 can further include an interface used for interacting with the three-dimensional medical image obtaining unit 130 and an interface used for interacting with the control console 210, etc.

For the convenience of understanding, a clinical surgical procedure will be described below briefly. In general, the clinical surgical procedure can include preoperative preparation, preoperative image scanning, preoperative surgical plan, intraoperative surgical navigation, postoperative surgical evaluation, etc. For example, the preoperative preparation includes: preparing devices in a navigation operating room, fixing the patient by a vacuum pad, and fixing the movement monitoring tools (or adhering mark points and the liked) on the body surface of the patient. For example, the preoperative image scanning includes carrying out preoperative CT scanning or MRI scanning on the patient. The preoperative surgical plan can include three-dimensional visualization of a medical image, three-dimensional reconstruction of an organ and focus, interactive surgical approach plan and surgical effect simulation and the like, wherein for example, the surgical approach plan can include selection of a needle entry point and a needle entry angle of the puncture needle; the surgical effect simulation can include thermal field simulation, damage field model reconstruction, etc. The intraoperative surgical navigation includes puncturing according to an approach in the surgical plan, etc. The postoperative surgical evaluation can include re-scanning a CT image or an MM image at specified time after the surgery, measuring the size of an actual injury area on the CT data and comparing the size with data calculated in the surgical plan to measure the accuracy and effect of the surgery.

The human organ movement monitoring method according to the embodiment of the present disclosure can be used in an intraoperative surgical navigation process, for example.

An exemplary surgical navigation process carried out in combination with a human body navigation system will be described below in combination with FIG. 3.

Figure 3:
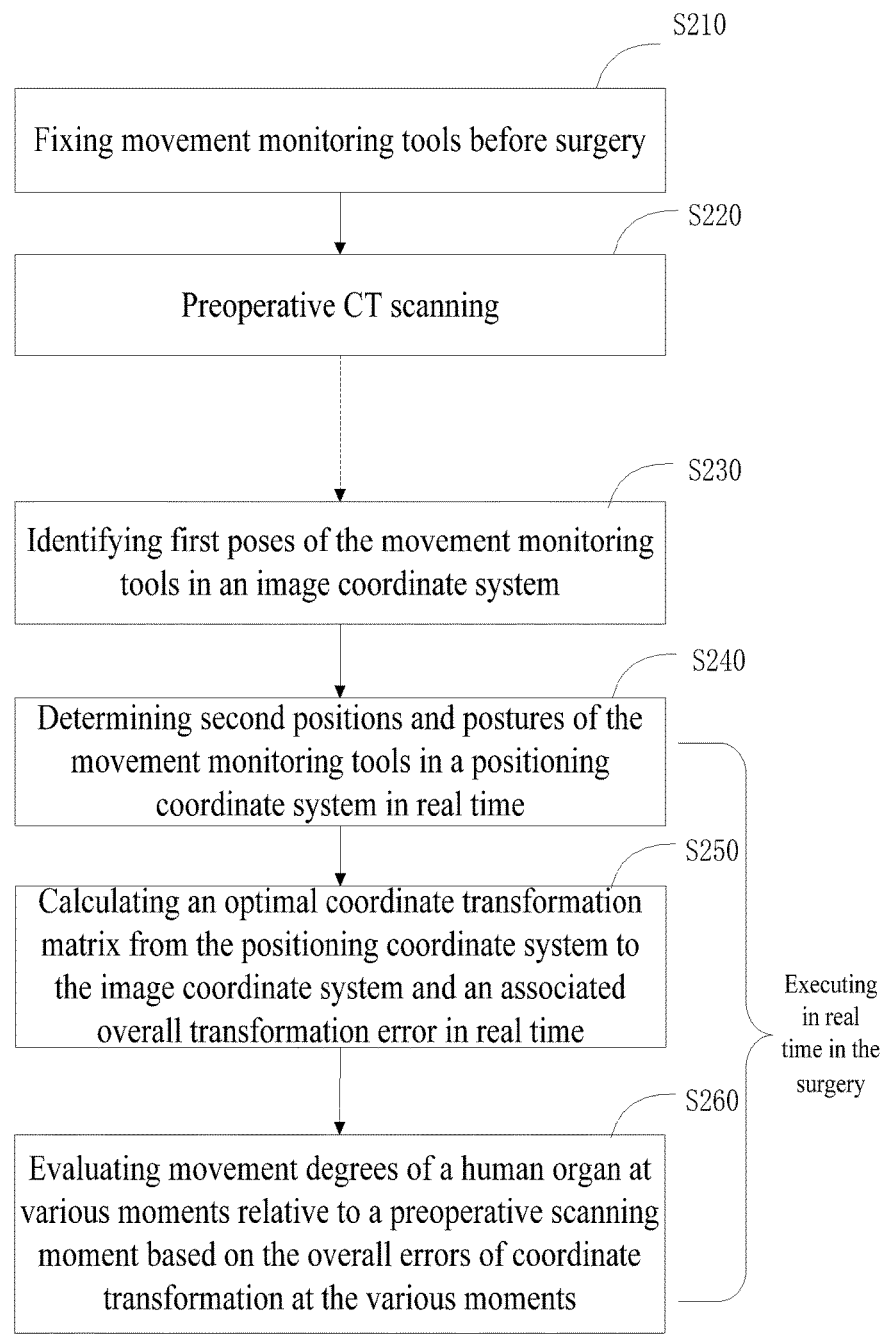
FIG. 3 shows an exemplary process of a surgical navigation method 200 according to an embodiment of the present disclosure.

FIG. 3 shows an exemplary process of a surgical navigation method 200 according to an embodiment of the present disclosure.

In a step S210, two or more movement monitoring tools are fixed on a patient body before the surgery.

In an example, 2-4 breath monitoring tools are placed on the body surface of the patient, the wearing positions are places greatly influenced by breath to the best, so that the relative positions of the several tools will generate relative change to a certain extent with the respiratory movement, the properties of the respiratory movement can be better represented by tracking the poses of the breath monitoring tools, and thus the properties of a target treatment part (focus) which moves with the respiratory movement can be better described.

However, the number of the breath monitoring tools is merely exemplary, and more breath monitoring tools can be selected as needed, for example, 5, 6 or more, etc.

In a step S220, a three-dimensional medical image of the treatment site of the patient fixed with the movement monitoring tools is obtained by preoperative scanning, the three-dimensional medical image having an associated image coordinate system. For example, the preoperative scanning can be CR scanning or MRI scanning. For example, the three-dimensional medical image is obtained by the three-dimensional medical image obtaining unit 130 as shown in FIG. 1 by reconstruction based on a CT scanning image data set.

After the three-dimensional medical image of the treatment site of the patient fixed with the movement monitoring tools is obtained by preoperative scanning, the three-dimensional medical image can be visually displayed on the display device, and the clinician can plan a surgical approach with reference to the three-dimensional medical image by means of a navigation software system, for example.

In a step S230, for example, the surgical navigation workstation 140 identifies first position and orientation of the movement monitoring tools in the image coordinate system from the preoperative three-dimensional medical image.

As mentioned above, mark points can be arranged on the movement monitoring tools, the mark points have image parameters which are obviously different from those of a human tissue in a CT image, so that the mark points can be manually or automatically identified from the CT image, and accordingly, the position and orientation of the movement monitoring tools in the image coordinate system can be identified.

It should be noted that the step S220 and the step S230 are connected by a dashed line arrow, which indicates that the two steps can be separated for a relatively long time, for example, several hours or several days.

In a step S240, in the surgery, in a state that the same movement monitoring tools are fixed on the body of the patient at the same position and orientation as in the preoperative scanning, second position and orientation of the movement monitoring tools in a positioning coordinate system are determined in real time, wherein the positioning coordinate system is a coordinate system which is referenced in a process of tracking the position and orientation of a surgical tool by the positioning device. For example, the second position and orientation of the movement monitoring tools in the positioning coordinate system are obtained by the positioning device and the positioning sensors on the movement monitoring tools as shown in FIG. 1 and are transmitted to the surgical navigation workstation 140.

In a step S250, the surgical navigation workstation calculates an optimal coordinate transformation relation between the positioning coordinate system and the image coordinate system in real time based on the first position and orientation of the movement monitoring tools in the image coordinate system and the second position and orientation thereof in the positioning coordinate system, and calculates overall errors of the movement monitoring tools during coordinate transformation from the positioning coordinate system to the image coordinate system based on the optimal coordinate transformation relation.

For introduction to coordinate transformation and error calculation, reference can be made to the instruction in the Section 6.4 in the doctoral dissertation entitled "RESEARCH ON KEY TECHNOLOGY OF COMPUTER ASSISTED INTERVENTIONAL OPERATION UNDER IMAGE GUIDANCE" of Zhai Weiming, the entire contents of which are herein incorporated by reference.

In a step S260, movement degree of a human organ at various moments relative to a preoperative scanning moment are evaluated based on the real-time determined overall errors of coordinate transformation of the movement monitoring tools at the various moments.

As mentioned above, in theory, in various stages of the respiratory movement cycle of the lung, if the movement state at a certain moment is closest to the movement state at the CT scanning moment, the mapping of the breath monitoring tool at the moment in the image coordinate system is closest to the pose of the breath monitoring tool in the image coordinate system obtained by the preoperative CT scanning, and thus the coordinate transformation error corresponding to the coordinate transformation matrix obtained by optimization at the moment in the surgery is the smallest.

Figure 4:
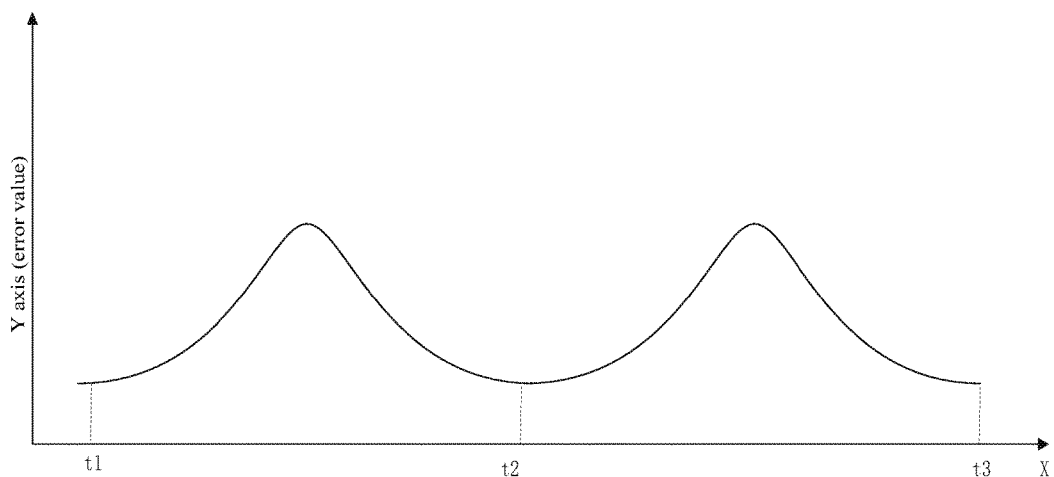
FIG. 4 shows a schematic diagram of a part of a time change curve of an overall error of coordinate transformation in a respiratory movement process.

FIG. 4 shows a schematic diagram of a part of a time change curve of an overall error of coordinate transformation in a respiratory movement process, wherein a horizontal axis represents time and a vertical axis represents an overall error of coordinate transformation. As shown in FIG. 4, at moments t1, t2, t3, the overall error of coordinate transformation is small, at this time, the breath state is close to the breath state at the preoperative scanning moment, the breath states at other moments deviate from the breath state at the preoperative scanning moment to different degrees, and the overall error of coordinate transformation changes accordingly.

By observing the change condition of the overall error of coordinate transformation with time in the surgical process, the difference degrees of the states of the human organ at the various moments relative to the preoperative scanning moment can be evaluated.

A human organ moment monitoring result in the embodiment of the present disclosure can be adopted in a variety of forms.

In an example, the real-time obtained time change curve of the overall error of coordinate transformation can be visually displayed on the display device in the form as shown in FIG. 4, for example. The clinician can determine the timing of, for example, puncturing the puncture needle in the patient by observing the time change curve of the overall error.

In an example, for example, the surgical navigation workstation in FIG. 1 determines the timing for the surgical tool to intervene in a human focus based on the evaluated movement degree of the human organ at the various moments relative to the preoperative three-dimensional scanning moment, and reminds a surgeon of the timing. In an example, when the overall error of coordinate transformation at a certain moment is 50% of the average overall error of coordinate transformation of a certain time period and the change trend is reduction, the certain moment is determined as the timing of the surgical tool for intervening the human focus, and then the timing information is displayed on the display device, for example, in a short message form or is output from a loudspeaker in a voice form to remind the clinician.

In an example, since the positioning coordinate system referred in the description of the poses of the breath monitoring tools is the coordinate system which is referenced in the process of positioning the position and orientation of the surgical tool, a moment when the pose of the human organ is basically uniform with the pose at the preoperative CT scanning moment can be determined on the basis of the evaluated movement (or difference) degrees of the pose of the human organ at various moments relative to the pose at the preoperative CT scanning moment, and the real-time tracked position of the surgical tool is transformed into the image coordinate system and is fused with the three-dimensional medical image by using the calculated coordinate transformation matrix from the positioning coordinate system to the image coordinate system at the moment, and then the fused image is visually displayed on the display device. Specifically, the human organ movement monitoring method may further include: determining a moment when the overall error of coordinate transformation is smaller than a preset threshold; determining a coordinate transformation matrix from the positioning coordinate system to the image coordinate system at the moment; and determining the position of the surgical tool in the image coordinate system based on the coordinate transformation matrix, and combining the image of the surgical tool with the three-dimensional medical image at the position and displaying the combined image on a display device. Namely, at the moment when the overall error of coordinate transformation is smaller than the preset threshold, the registration from the positioning coordinate system where the surgical tool is located to the image coordinate system is carried out, the image of the surgical tool is fused with the human three-dimensional model based on the position of the surgical tool tracked by the positioning device 110 for example, and is visually displayed on the display device to assist the surgery of the clinician.

It should be noted that the breath monitoring process can be continuously carried out in the surgery.

In addition, a rule obtained by breath monitoring, for example, the information of a time interval (as shown in FIG. 4) between a former moment having the smallest overall error and a moment having the smallest overall error can also be provided for the clinician, to enable the clinician to make psychological preparation and operation preparation before puncturing the needle at the next time.

By adopting the surgical navigation system and the human organ movement monitoring method, the movement degree (or difference degree) of the state of the human organ relative to the state at the CT scanning moment can be monitored without using a special human organ monitor, for example, for the respiratory movement, no special respiratory gate control device is needed. But, the present disclosure does not exclude use in cooperation with the special human organ monitor.

The surgical navigation system and the human organ movement monitoring method in the embodiment of the present disclosure do not simply consider the human body as a rigid body for carrying out registration on the preoperative positioning coordinate system and the image coordinate system, but consider the internal movement of the human body for monitoring the difference degree of the state of the human organ relative to the state at the CT scanning moment, so that the doctor can be reminded of a proper timing for operation and can execute the preoperative surgical plan more accurately, and the dependence on the individual experience of the clinician is reduced.

In addition, the embodiment of the disclosure can take the form of a computer program product. The computer program product can be accessed via a computer readable medium, for use by or in combination with a computer or any instruction execution system. The computer readable medium can include a device for storing, exchanging, transmitting or sending a program. The computer readable medium can be an electronic, magnetic, optical, electromagnetic, infrared or semiconductor system (or device or apparatus) or a transmission medium. Examples of the computer readable medium include a semiconductor or a solid-state memory, a magnetic tape, a detachable computer floppy disk, a random access memory (RAM), a read-only memory (ROM), a magnetic disk or an optical disk.

Various embodiments of the present disclosure have been described above, and the foregoing description is exemplary, rather than exhaustive, and is not limited to the disclosed embodiments. Many modifications and variations are obvious for those of ordinary skill in the art without departing from the scope or spirit of the illustrated embodiments. The selection of terms herein is intended to explain the principles of the embodiments, practical application or improvements in the technologies on the market to the best, or enable others of ordinary skill in the art to understand the embodiments disclosed herein.

The invention claimed is:

1. A human organ movement monitoring method for monitoring movement of a human organ of a patient in a surgical process in real time, wherein a preoperative three-dimensional medical image of a treatment site of a patient whose body surface is fixed with two or more movement monitoring tools is obtained by a preoperative scanning prior to the surgery, the three-dimensional medical image having an associated image coordinate system, wherein the human organ movement monitoring method for monitoring the movement of the human organ of the patient is based on position and orientation of the two or more movement monitoring tools fixed on the patient's body surface and comprises the following steps:

obtaining a first position and orientation of each movement monitoring tool in the image coordinate system identified from the preoperative three-dimensional medical image;

in a state that the same movement monitoring tools are fixed on the body of the patient at the same position and orientation as in the preoperative scanning, determining a second position and orientation of each movement monitoring tool in a positioning coordinate system in real time, wherein the positioning coordinate system is a coordinate system which is referenced in a process of positioning the position and orientation of a surgical tool;

calculating a coordinate transformation between the positioning coordinate system and the image coordinate system in real time based on the first position and orientation of each movement monitoring tool in the image coordinate system and the second position and orientation thereof in the positioning coordinate system;

calculating a plurality of overall errors of the coordinate transformation between the positioning coordinate system and the image coordinate system at a plurality of moments;

evaluating a movement degree of the human organ of the patient at the plurality of moments relative to a preoperative scanning moment based on the calculated overall errors of the coordinate transformation at the plurality of moments, determining, from the plurality of moments, a moment when the overall error of coordinate transformation is smaller than a preset threshold;

determining a coordinate transformation matrix between the positioning coordinate system and the image coordinate system based on the first position and orientation of each movement monitoring tool in the image coordinate system and the second position and orientation thereof in the positioning coordinate system at the determined moment;

determining the position of the surgical tool in the image coordinate system based on the coordinate transformation matrix;

determining a timing for the surgical tool to intervene in a human focus based on the evaluated movement degree of the human organ at the plurality of moments relative to the preoperative three-dimensional scanning moment; and reminding a surgeon of the timing, wherein each movement monitoring tool is provided with at least four mark points capable of being tracked by a positioning device, in which any three arbitrary mark points are non-collinear, wherein the first position and orientation of the movement monitoring tools in the image coordinate system are identified by identifying the mark points of each movement monitoring tool in the three-dimensional medical image; and the second position and orientation of the movement monitoring tools in the positioning coordinate system are determined by tracking the mark points of each movement monitoring tool in the surgery through the positioning device.

2. The human organ movement monitoring method of claim 1, wherein the human organ movement comprises various stages of a respiratory cycle of a lung.

3. The human organ movement monitoring method of claim 1, further comprising:
combining the image of the surgical tool with the three-dimensional medical image at the determined position to obtain a combined image; and
displaying the combined image on a display device.

4. The human organ movement monitoring method of claim 1, wherein the surgical tool is a puncture needle.

5. The human organ movement monitoring method of claim 1, wherein the position and orientation of each movement monitoring tool fixed on the patient body are greatly influenced by the human organ movement.

6. The human organ movement monitoring method of claim 1, wherein the positioning device is an electromagnetic tracker.

7. A surgical navigation system, comprising:
a positioning device for tracking position and orientation of a surgical tool and movement monitoring tools in a positioning coordinate system;
two or more movement monitoring tools, which are fixed on a patient's body surface, and the position and orientation of which in the positioning coordinate system are capable of being tracked by the positioning device for evaluating a movement state of a human organ of the patient;
a processor, and memory that stores instructions, wherein the instructions, when executed by the processor, perform: obtaining a preoperative three-dimensional medical image of a treatment site of the patient whose body surface is fixed with the movement monitoring tools, the three-dimensional medical image having an associated image coordinate system;
a surgical navigation workstation for registering and combining the preoperative three-dimensional medical image with an intraoperative surgical tool image and visually displaying the same on a connected display device to guide the surgical operation of a surgeon;
wherein the surgical navigation workstation further monitors the movement state of the human organ of the patient based on the position and orientation of the two or more movement monitoring tools fixed on the patient's body surface through the following operations:
identifying a first position and orientation of each of the movement monitoring tools in the image coordinate system from the preoperative three-dimensional medical image;
determining a second position and orientation of each of the movement monitoring tools in the positioning coordinate system in the surgery in real time;
calculating a coordinate transformation between the positioning coordinate system and the image coordinate system in real time based on the first position and orientation of the movement monitoring tools in the image coordinate system and the second position and orientation thereof in the positioning coordinate system;
calculating a plurality of overall errors of the coordinate transformation between the positioning coordinate system and the image coordinate system at a plurality of moments;
evaluating a movement degree of the human organ of the patient at the plurality of moments relative to a preoperative scanning moment based on the calculated overall errors of the coordinate transformation at the plurality of moments,
determining, from the plurality of moments, a moment when the overall error of coordinate transformation is smaller than a preset threshold;
determining a coordinate transformation matrix between the positioning coordinate system and the image coordinate system based on the first position and orientation of each movement monitoring tool in the image coordinate system and the second position and orientation thereof in the positioning coordinate system at the determined moment;
determining the position of the surgical tool in the image coordinate system based on the coordinate transformation matrix;
determining a timing for the surgical tool to intervene in a human focus based on the evaluated movement degree of the human organ at the plurality of moments relative to the preoperative three-dimensional scanning moment; and
reminding a surgeon of the timing,
wherein each movement monitoring tool is provided with at least four mark points capable of being tracked by a positioning device, in which any three arbitrary mark points are non-collinear, wherein the first position and orientation of the movement monitoring tools in the image coordinate system are identified by identifying the mark points of each movement monitoring tool in the three-dimensional medical image; and the second position and orientation of the movement monitoring tools in the positioning coordinate system are determined by tracking the mark points of each movement monitoring tool in the surgery through the positioning device.

8. The surgical navigation system of claim 7, wherein the human organ movement comprises various stages of a respiratory cycle of a lung.

9. The surgical navigation system of claim 7, wherein the surgical navigation workstation is further configured to:
combining the image of the surgical tool with the three-dimensional medical image at the determined position to obtain a combined image; and displaying the combined image on a display device.

10. The surgical navigation system of claim 7, wherein the surgical tool is a puncture needle.

11. The surgical navigation system of claim 7, wherein the position and orientation of each movement monitoring tool fixed on the patient body are greatly influenced by the movement state of the human organ of the patient.

12. A non-transitory computer readable medium, on which a computer program is recorded, the computer program being used in combination with a surgical navigation system and executing the following operations for monitoring a movement state of a human organ of a patient based on position and orientation of two or more movement monitoring tools fixed on the patient's body surface, when being executed by a processing device:

obtaining a first position and orientation of each of the movement monitoring tools in an image coordinate system identified from a preoperative three-dimensional medical image, wherein the preoperative three-dimensional medical image is obtained by scanning a treatment site of a patient whose body surface is fixed with two or more movement monitoring tools prior to the surgery, the three-dimensional medical image having an associated image coordinate system;

in a state that the same movement monitoring tools are fixed on the body of the patient at the same position and orientation as in the preoperative scanning, determining a second position and orientation of each of the movement monitoring tools in a positioning coordinate system in real time, wherein the positioning coordinate system is a coordinate system which is referenced in a process of positioning the position and orientation of a surgical tool;

calculating a coordinate transformation between the positioning coordinate system and the image coordinate system in real time based on the first position and orientation of the movement monitoring tools in the image coordinate system and the second position and orientation thereof in the positioning coordinate system;

calculating a plurality of overall errors of the coordinate transformation between the positioning coordinate system and the image coordinate system at a plurality of moments; and evaluating a movement degree of the human organ of the patient at the plurality of moments relative to a preoperative scanning moment based on the calculated overall errors of coordinate transformation at the plurality of moments, determining, from the plurality of moments, a moment when the overall error of coordinate transformation is smaller than a preset threshold;

determining a coordinate transformation matrix between the positioning coordinate system and the image coordinate system based on the first position and orientation of each movement monitoring tool in the image coordinate system and the second position and orientation thereof in the positioning coordinate system at the determined moment;

determining the position of the surgical tool in the image coordinate system based on the coordinate transformation matrix;

determining a timing for the surgical tool to intervene in a human focus based on the evaluated movement degree of the human organ at the plurality of moments relative to the preoperative three-dimensional scanning moment; and reminding a surgeon of the timing, wherein each movement monitoring tool is provided with at least four mark points capable of being tracked by a positioning device, in which any three arbitrary mark points are non-collinear, wherein the first position and orientation of the movement monitoring tools in the image coordinate system are identified by identifying the mark points of each movement monitoring tool in the three-dimensional medical image; and the second position and orientation of the movement monitoring tools in the positioning coordinate system are determined by tracking the mark points of each movement monitoring tool in the surgery through the positioning device.

13. The non-transitory computer readable medium of claim 12, wherein the computer program further executes the following operations when being executed by the processing device:

combining, based on the position and orientation, the image of the surgical tool with the three-dimensional medical image, and displaying the combined image on a display device.

14. The non-transitory computer readable medium of claim 12, wherein the human organ movement comprises various stages of a respiratory cycle of a lung.

* * * * *